United States Patent [19]

Berthold

[11] 4,129,658

[45] Dec. 12, 1978

[54] 4-STYRYL-HEXAHYDRO-4-INDOLINOLS

[75] Inventor: Richard Berthold, Bottmingen, Switzerland

[73] Assignee: Sandoz Ltd., Basel, Switzerland

[21] Appl. No.: 834,103

[22] Filed: Sep. 19, 1977

[30] Foreign Application Priority Data

Sep. 22, 1976 [CH] Switzerland ............... 12001/76

[51] Int. Cl.² .................. A61K 31/415; C07D 209/04; C07D 405/06
[52] U.S. Cl. ................................. 424/274; 542/429; 542/430
[58] Field of Search ............... 542/429, 430; 424/274

[56] References Cited

U.S. PATENT DOCUMENTS 3,635,956  1/1972  Krapcho .............................. 424/274

FOREIGN PATENT DOCUMENTS 836290  12/1975  Belgium.
855168  11/1977  Belgium.
7704839  5/1976  Netherlands.

*Primary Examiner*—Donald B. Moyer
*Attorney, Agent, or Firm*—Gerald D. Sharkin; Richard E. Vila; Frederick H. Weinfeldt

[57] ABSTRACT

The present invention provides compounds of formula I,

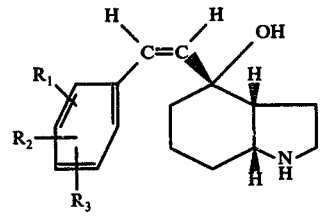

wherein
  $R_1$ and $R_2$ are, independently, hydrogen, fluorine, chlorine, trifluoromethyl, alkyl of 1 to 4 carbon atoms, or alkoxy of 1 to 4 carbon atoms, and
  $R_3$ is hydrogen, or alkoxy of 1 to 4 carbon atoms, with the proviso that when $R_3$ is alkoxy then at least one of $R_1$ and $R_2$ is alkoxy, or
  $R_1$ and $R_2$ are bound to adjacent ring carbon atoms and are together $-(CH_2)_m-$, wherein m is 3 or 4, $-CH=CH-CH=CH-$, or $-O-CH_2-X-$, wherein X is $-O-$ or $-CH_2-$, and
  $R_3$ is hydrogen, fluorine, chlorine, trifluoromethyl, alkyl of 1 to 4 carbon atoms, or alkoxy of 1 to 4 carbon atoms, useful as hypolipidemic agents and anti-arrhythmics.

36 Claims, No Drawings

4-STYRYL-HEXAHYDRO-4-INDOLINOLS

The present invention relates to perhydroindolinols.

The present invention provides compounds of formula I,

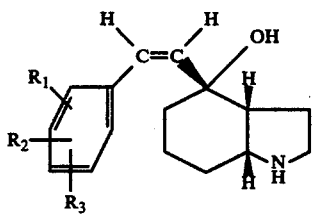

wherein
$R_1$ and $R_2$ are, independently, hydrogen, fluorine, chlorine, trifluoromethyl, alkyl of 1 to 4 carbon atoms, or alkoxy of 1 to 4 carbon atoms, and
$R_3$ is hydrogen, or alkoxy of 1 to 4 carbon atoms, with the proviso that when $R_3$ is alkoxy then at least one of $R_1$ and $R_2$ is alkoxy, or
$R_1$ and $R_2$ are bound to adjacent ring carbon atoms and are together —$(CH_2)_m$—, wherein $m$ is 3 or 4, —CH=CH—CH=CH—, or —O—$CH_2$—X—, wherein X is —O— or —$CH_2$—, and
$R_3$ is hydrogen, fluorine, chlorine, trifluoromethyl, alkyl of 1 to 4 carbon atoms, or alkoxy of 1 to 4 carbon atoms.

In formula I, the phenyl ring and the 4-indolinyl nucleus are cis to each other. When $R_1$ and $R_2$ are together —CH=CH—CH=CH—, it is to be appreciated that the phenyl ring becomes a naphthyl nucleus.

Any alkyl or alkoxy radical has preferably 2 carbon atoms, or especially 1 carbon atom. When $R_1$ and $R_2$ are together —$(CH_2)_m$—, —CH=CH—CH=CH— or —O—$CH_2$—X—, $R_3$ is preferably hydrogen.

When $R_1$ and $R_2$ are fluorine, chlorine or alkyl, these are preferably identical. When there are two or three alkoxy groups present these are preferably identical. When both of $R_1$ and $R_2$ are either fluorine or trifluoromethyl; these are preferably bound to ring carbon atoms which are meta and para to the double bond, and are preferably meta to each other.

The present invention provides a process for the production of a compound of formula I, as defined above, which comprises deprotecting a compound of formula II,

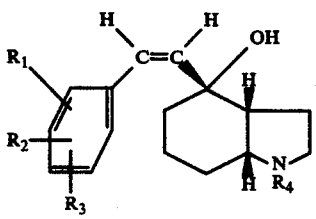

wherein
$R_1$, $R_2$ and $R_3$ are as defined above, and
$R_4$ is a protecting group.

The process may be effected in conventional manner for splitting off of amino protecting groups from similar cyclic amines, e.g. through solvolysis, especially hydrolysis. Suitable groups $R_4$ include aryloxycarbonyl, arylalkyloxycarbonyl or alkoxycarbonyl groups of up to 12 carbon atoms such as ethoxycarbonyl or methoxycarbonyl.

Preferably the reaction is effected under strongly basic conditions. A solvent system such as methanol/water or DMSO/methanol may be used. Suitable reaction temperatures may be from 50° to 250° C. The reaction may be effected in an autoclave.

Free base forms of the compounds of formula I may be converted into acid addition salt forms in conventional manner and vice versa. Suitable acids for salt formation include fumaric acid, malonic acid, and maleic acid.

Compounds of formula II may be obtained by reducing a compound of formula III,

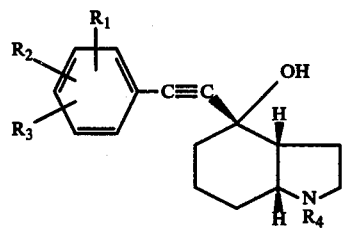

wherein $R_1$, $R_2$, $R_3$ and $R_4$ are as defined above, in conventional manner, e.g. by hydrogenolysis in the presence of a Lindlar catalyst.

Compounds of formula III may be obtained by condensing a compound of formula IV,

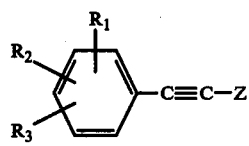

wherein
$R_1$, $R_2$ and $R_3$ are as defined above, and
Z is Li, MgCl, MgBr or MgI,
with a compound of formula V,

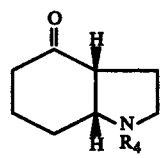

wherein $R_4$ is as defined above.

Insofar as the production of any particular starting material is not described, this is known or may be prepared in conventional manner.

In the following Examples all temperatures are in degrees Centigrade and are uncorrected.

EXAMPLE 1

(3aRS, 4RS, 7aRS)-4-(3,4-dimethoxy-(Z)-styryl)-hexahydro-4-indolinol 30 g of (3aRS, 4RS, 7aRS)-4-(3,4-dimethoxy-(Z)-styryl)-hexahydro-4-hydroxy-1-indoline carboxylic acid ethyl ester are heated in 145 ml methanol, 145 ml dimethyl sulphoxide and 300 ml 30% (w/v) NaOH for 16 hours at 95°. The mixture is poured into ice water and the aqueous phase extracted with ether. The ether phase is extracted with 2 N tartaric acid solution. The acidic extract is made alkaline and continuously extracted with methylene chloride. The methylene chloride extract is dried over magnesium sulphate, filtered and concentrated. The residue (the title compound in free base form) is converted into the hydrogen maleate of the title compound; M.Pt. 219°–220°.

The starting material is obtained as follows:

a. A solution of 25.8 g cis-perhydro-4-oxo-1-indoline carboxylic acid ethyl ester in 200 ml absolute tetrahydrofuran is added at −30° to −40° to 1 mole of lithium 3,4-dimethoxyphenylacetylide in tetrahydrofuran (formed from 2 moles 2 molar butyl lithium in hexane and 1 mole 1-(2,2-dibromovinyl)-3,4-dimethoxybenzene in 300 ml benzene at −70°). The mixture is stirred over-night. 100 ml concentrated ammonium chloride solution is added with ice cooling. The organic phase is worked up to give (3aRS, 4RS, 7aRS)-4-(3,4-dimethoxy)-phenylethinyl-hexahydro-4-hydroxy-1-indoline carboxylic acid ethyl ester; M.Pt. 153°–155° (from ether).

b. 23.4 g (3aRS, 4RS, 7aRS)-(3,4-dimethoxy)-phenylethinyl-hexahydro-4-hydroxy-1-indoline carboxylic acid ethyl ester in 370 ml benzene is hydrogenated in the presence of Lindlar catalyst poisoned with 3 ml of 5% (v/v) quinoline solution in benzene. After filtration (3aRS, 4RS, 7aRS)-4-(3,4-dimethoxy-(Z)-styryl)-hexahydro-4-hydroxy-1-indoline carboxylic acid ethyl ester is obtained as an oil, after working up.

In analogous manner to that described in Example 1 from the appropriate compounds of formlae II and III, wherein $R_4$ is ethoxycarbonyl, the following compounds of formula I are obtained, wherein

| EXAMPLE No. | $R_1$ | $R_2$ | $R_3$ | M.Pt. |
|---|---|---|---|---|
| 2 | 4-CH$_3$ | H | H | 88° – 90° [1) / 108° – 110° [2) |
| 3 | 4-CH$_3$O | H | H | 183° – 185° [3)4) |
| 4 | 4-Cl | H | H | 222° – 224° [4)5) |
| 5 | 2-Cl | H | H | 191° – 193° [6) |
| 6 | H | H | H | 222° – 223° [5)7) |
| 7 | 2-Cl | 6-Cl | H | 159° – 162° [1) |
| 8 | 3-CF$_3$ | H | H | 202° – 203° [5) |
| 9 | 3-CH$_3$O | H | H | 154° – 156° [3) |
| 10 | 4-F | H | H | 210° – 212° [5) |
| 11 | 3-Cl | 4-Cl | H | 206° – 208° [5) |
| 12 | 3-CH$_3$O | 4-CH$_4$O | 5-CH$_3$O | 112° – 114° [1) |
| 13 | 2,3-CH=CH—CH=CH— | | H | 115° – 117° [1) |
| 14 | 3,4-O—CH$_2$—O— | | H | 154° – 156° [3) |
| 15 | 3-CH$_3$ | 4-CH$_3$ | H | |

[1) free base
[2) hydrogen malonate
[3) bis[base]malonate
[4) decomposition
[5) bis[base]fumarate
[6) hydrogen fumarate
[7) M.Pt. of corresponding formula III compound 104° – 105°

In analogous manner the following compounds of formula I may also be prepared:

| | $R_1$ | $R_2$ | $R_3$ |
|---|---|---|---|
| a) | 2,3-O—CH$_2$—CH$_2$— | | 4-F |
| b) | 2,3-CH$_2$—CH$_2$—O— | | 4-C$_2$H$_5$ |
| c) | 3,4-(CH$_2$)$_4$— | | 5-CF$_3$ |
| d) | 3,4-CH=CH—CH=CH— | | 2-C$_2$H$_5$O |

The compounds of formula I are useful because they possess pharmacological activity in animals as hypolipidemic agents, e.g. for the treatment or prophylaxis of diseases connected with high cholesterol contents or total lipid contents in the blood, e.g. arteriosclerosis coronary sclerosis or essential hyperlipidemia, as indicated by the fall in cholesterol and triglyceride levels in the blood of male albino Wistar rats weighing 110–130 g initially. The rats are maintained on drug-free laboratory chow diet for seven days and then divided into groups of 8 to 10 animals. Each group with the exception of the control is then given orally 30 to 250 mg/kg animal body weight per diem of the compound for 6 days. At the end of this period, the animals are anesthetized with sodium hexobarbital and bled from the carotid arteries. Serum or plasma samples are collected, and 1.0 ml samples of the serum are added to 9.0 ml redistilled isopropanol. Two autoanalyzer cupsful of a mixture of zeolite-copper hydroxide and Lloydds reagent (Kessler, G., and Lederer, H, 1965, Technicon Symposium, Mediad Inc., New York [345, 347]) are added, and the mixture is shaken for 1 hour. Cholesterol and triglyceride levels are determined simultaneously on the same sample by Technicon N-24 (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

The hypolipidemic effective dosage of compounds I employed in the alleviation of lipidemia may vary depending on the particular compound employed and the severity of the condition being treated. However, in general, satisfactory results are obtained when the compounds of formula I are administered at a daily dosage of from about 2 milligrams to about 100 milligrams per kilogram of animal body weight (e.g. 2–10 mg/kg) given in divided doses two to four times a day, or in sustained release form. For most large mammals, the total daily dosage is from about 100 milligrams to about 1000 milliigrams. Dosage forms suitable for internal use comprise from about 25 to about 500 milligrams of the active compound in intimate admixture with a solid or liquid pharmaceutically acceptable carrier or diluent.

The compounds of Examples 1 to 6 have been found to be effective hypolipidemic agents in rats at doses of 30 mg/kg animal body weight.

The compounds of formula I are furthermore useful as anti-arrhythmic agents, e.g. for the treatment of heart rhythm disorders, as indicated by an inhibition of chloroform induced arrhythmia in mice on i.p. administration of from 6.25 to 50 mg/kg animal body weight of this compounds in accordance with the principles of J. W. Lawson, J. Pharmacolog. Exp. Therap. (1968) 160, 22-31.

For this use the dosage will, of course, vary depending on the compound employed, mode of administration and treatment desired. However, in general, satisfactory results are obtained when administered at a daily dosage of from about 0.01 mg to about 50 mg per kg animal body weight, conveniently given in divided doses 2 to 4 times a day or in sustained release form. For the larger mammals, the total daily dosage is in the range of from about 1 to about 100 mg, and dosage forms suitable for oral administration comprise from about 0.2 mg to about 50 mg of the compounds admixed with a solid or liquid pharmaceutical carrier or diluent.

The hypolipidemic use is the preferred use. The Example 1 compound is the most interesting compound for the hypolipidemic utility.

In a class of compounds $R_1$, $R_2$ and $R_3$ are as defined above, with the proviso that $R_1$ and $R_2$ when defined together are other than —O—CH$_2$—X—.

In a group of compounds $R_1$ and $R_2$ are chosen from H, CH$_3$ or CH$_3$O. In another group of compounds $R_3$ is H or CH$_3$O.

The compounds of formula I may be administered in pharmaceutically acceptable acid addition salt form. Such acid addition salt forms exhibit the same order of activity as the free base forms. The present invention also provides a pharmaceutical composition comprising a compound of formula I, in free base form or in pharmaceutically acceptable acid addition salt form, in association with a pharmaceutical carrier or diluent. Such compositions may be made in conventional manner so as to be, for example, a solution or a tablet.

I claim:

1. A compound of formula I,

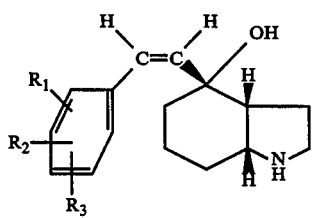

wherein
$R_1$ and $R_2$ are, independently, hydrogen, fluorine, chlorine, trifluoromethyl, alkyl of 1 to 4 carbon atoms, or alkoxy of 1 to 4 carbon atoms, and
$R_3$ is hydrogen, or alkoxy of 1 to 4 carbon atoms, with the proviso that when $R_3$ is alkoxy then at least one of $R_1$ and $R_2$ is alkoxy, or
$R_1$ and $R_2$ are bound to adjacent ring carbon atoms and are together —(CH$_2$)$_m$—, wherein $m$ is 3 or 4, —CH=CH—CH=CH—, or —O—CH$_2$—X—, wherein X is —O— or —CH$_2$—, and
$R_3$ is hydrogen, fluorine, chlorine, trifluoromethyl, alkyl of 1 to 4 carbon atoms, or alkoxy of 1 to 4 carbon atoms,
or a pharmaceutically acceptable acid addition salt thereof.

2. A compound of claim 1 in which any alkyl or alkoxy radical has 1 or 2 carbon atoms.

3. A compound of claim 1 in which any alkyl or alkoxy radical has 1 carbon atom.

4. A compound of claim 1 in which $R_1$ and $R_2$ are identical when they are fluorine, chlorine, or alkyl.

5. A compound of claim 1 in which alkoxy groups are identical when there are two or three such groups present.

6. A compound of claim 1 in which $R_1$ and $R_2$ when defined together are other than O—CH$_2$—X—.

7. A compound of claim 1 in which $R_1$ and $R_2$ are chosen from the group of hydrogen, methyl or methoxy.

8. A compound of claim 1 in which $R_3$ is hydrogen or methoxy.

9. A compound of claim 1 in free base form.

10. A compound of claim 1 in the form of a pharmaceutically acceptable acid addition salt.

11. The compound of claim 1 which is (3aRS, 4RS, 7aRS)-4-(3,4-dimethoxy-(Z)-styryl)-hexahydro-4-indolinol.

12. The compound of claim 1 which is the hydrogen maleate salt of (3aRS, 4Rs, 7aRS)-4-(3,4-dimethoxy-(Z)-styryl)-hexahyro-4-indolinol.

13. The compound of claim 1 wherein $R_1$, $R_2$ and $R_3$ are respectively 4—CH$_3$, H and H.

14. The compound of claim 1, wherein $R_1$, $R_2$ and $R_3$ are respectively 4—CH$_3$O, H and H.

15. The compound of claim 1, wherein $R_1$, $R_2$ and $R_3$ are respectively 4—Cl, H and H.

16. The compound of claim 1, wherein $R_1$, $R_2$ and $R_3$ are respectively 2—Cl, H and H.

17. The compound of claim 1, wherein $R_1$, $R_2$ and $R_3$ are respectively H, H and H.

18. The compound of claim 1, wherein $R_1$, $R_2$, and $R_3$ are respectively 2—Cl, 6—Cl and H.

19. The compound of claim 1, wherein $R_1$, $R_2$ and $R_3$ are respectively 3—CF$_3$, H and H.

20. The compound of claim 1, wherein $R_1$, $R_2$ and $R_3$ are respectively 3—CH$_3$O, H and H.

21. The compound of claim 1, wherein $R_1$, $R_2$ and $R_3$ are respectively 4—F, H and H.

22. The compound of claim 1, wherein $R_1$, $R_2$ and $R_3$ are respectively 3—Cl, 4—Cl and H.

23. The compound of claim 1, wherein $R_1$, $R_2$ and $R_3$ are respectively 3—CH$_3$O, 4—CH$_4$O and 5—CH$_3$O.

24. A compound of claim 1 in which $R_3$ is hydrogen when $R_1$ and $R_2$ are together —(CH$_2$)$_m$—, —CH=CH—CH=CH— or O—CH$_2$—X—.

25. A compound of claim 24, wherein $R_1$ and $R_2$ together are 2,3—CH=CH—CH=CH—.

26. A compound of claim 24, wherein $R_1$ and $R_2$ together are 3,4—O—CH$_2$—O—.

27. A pharmaceutical composition useful in treating lipidemia which comprises a compound of claim 1 or a pharmaceutically acceptable acid addition salt thereof in an amount effective in obtaining a hypolipidemic effect, in association with a pharmaceutical carrier or diluent.

28. A composition of claim 27 in which the compound or salt is present in an amount of from about 25 milligrams to about 500 milligrams.

29. A composition of claim 28 in which the compound is (3aRS, 4RS, 7aRS)-4-(3,4-dimethoxy-(Z)-styryl)-hexahydro-4-indolinol.

30. A pharmaceutical composition useful in treating arrhythmia which comprises a compound of claim 1 or a pharmaceutically acceptable acid addition salt thereof in an amount effective in obtaining a arrhymthmic effect, in association with a pharmaceutical carrier or diluent.

31. A composition of claim 30 in which the compound or salt is present in an amount of from about 0.2 milligram to about 50 milligrams.

32. A method of obtaining a hypolipidemic effect in a mammal in need of such treatment which comprises administering to said mammal a hypolipidemic-effective amount of a compound of claim 1 or a pharmaceutically acceptable acid addition salt thereof.

33. A method of claim 32 in which the compound or salt is administered orally in an amount of from about 100 milligrams to about 1000 milligrams daily.

34. A method of claim 33 in which the compound is (3aRS, 4RS, 7aRS)-4-(3,4-dimethoxy-(Z)-styryl)-hexahydro-4-indolinol.

35. A method of obtaining an anti-arrhythmic effect in a mammal in need of such treatment which comprises administering to said mammal an anti-arrhythmic-effective amount of a compound of claim 1 or a pharmaceutically acceptable acid addition salt thereof.

36. A method of claim 35 in which the compound or salt is administered orally in an amount of from about 1 milligram to about 100 milligrams daily.

* * * * *